United States Patent [19]

Pollock

[11] Patent Number: 5,413,577
[45] Date of Patent: May 9, 1995

[54] ANATOMICAL PRECONTOURED PLATING

[76] Inventor: Richard A. Pollock, 5260 Riverview Rd., NW., Atlanta, Ga. 30327

[21] Appl. No.: 582,761

[22] Filed: Sep. 14, 1990

Related U.S. Application Data

[63] Continuation of Ser. No. 518,221, May 3, 1990, Pat. No. 4,966,599, which is a continuation of Ser. No. 274,699, Nov. 15, 1988, abandoned, which is a continuation of Ser. No. 35,658, Apr. 7, 1987, abandoned.

[51] Int. Cl.$^6$ ............................................. A61B 17/00
[52] U.S. Cl. ...................................... 606/69; 606/53
[58] Field of Search ..................... 606/69, 70, 71, 77, 606/53, 60, 62, 64, 65, 72, 73, 74, 76

[56] References Cited

U.S. PATENT DOCUMENTS 4,781,183  11/1988  Casey et al. ................ 606/77 X
4,905,680  3/1990   Tunc ........................... 606/77 X

OTHER PUBLICATIONS

Vitallium Skull Plates, Fred W. Geib, M.D., 1941.

Primary Examiner—Sam Rimell
Attorney, Agent, or Firm—Kilpatrick & Cody

[57] ABSTRACT

Precontoured plating, screws, instruments and methods for osteosynthesis. Plates according to the present invention take advantage of the fact that human adult craniofacial structure and shape is highly similar among the population. The plates are thus preformed, pretempered, precontoured, and preconfigured during manufacture to fit a large proportion of the human adult population. The plates consequently require less time during surgery to twist and bend to conform to the skeletal structure and their crystalline and other structural characteristics need not be adversely affected by extensive bending, twisting and shaping in the operating room. The plates may be packaged and presented for use on forms which simulate portions of the skull so that their intended craniofacial location is easily recognized by members of the surgical team. Because bone thickness at particular craniofacial skeletal locations is highly consistent in the adult population, appropriate length screws may also be packaged with the plates with which they are to be used, as for instance, by insertion through the plates on the skeletal-shaped packaging form. The packaging also allows the plates to be pre-sterilized to save time which would otherwise be used for sterilizing the plates. Screws, screw transport units and starters and dispensers for the plates and screws are also disclosed.

8 Claims, 10 Drawing Sheets

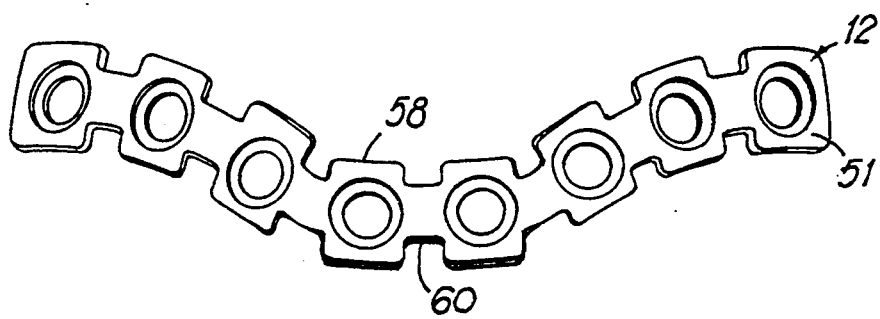
FIG. 11A
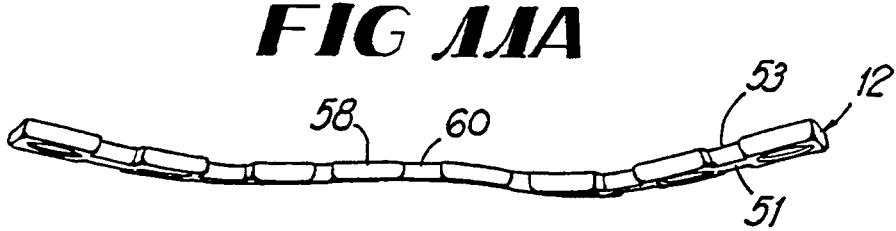
FIG. 11B
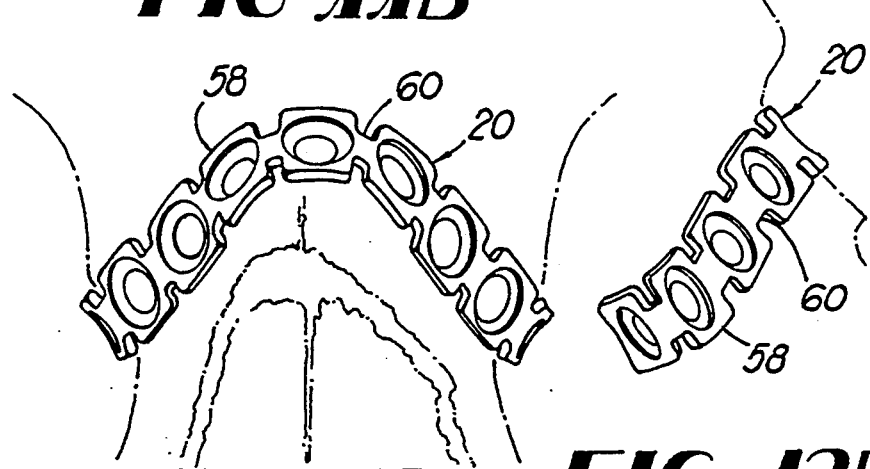
FIG. 12A     FIG. 12B
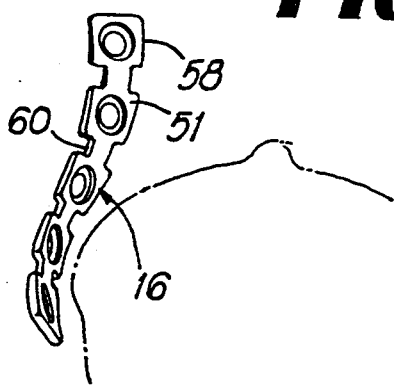
FIG. 13
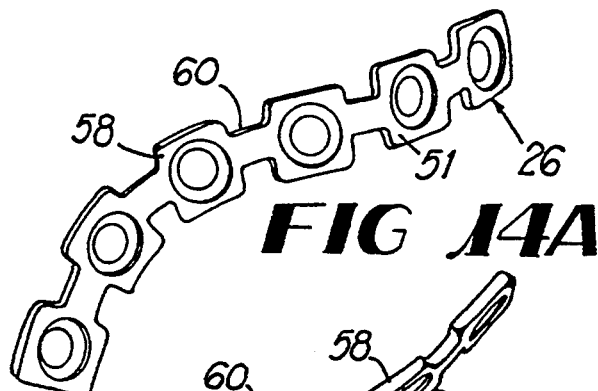
FIG. 14A
FIG. 14B

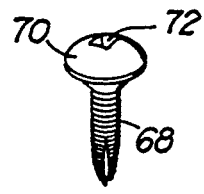
FIG 22
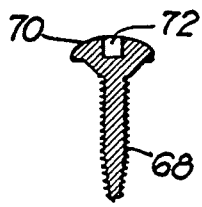
FIG 23
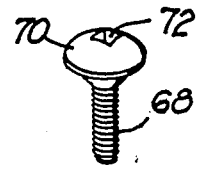
FIG 24
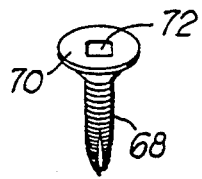
FIG 25
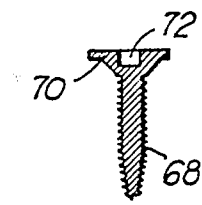
FIG 26
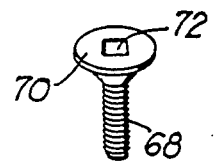
FIG 27
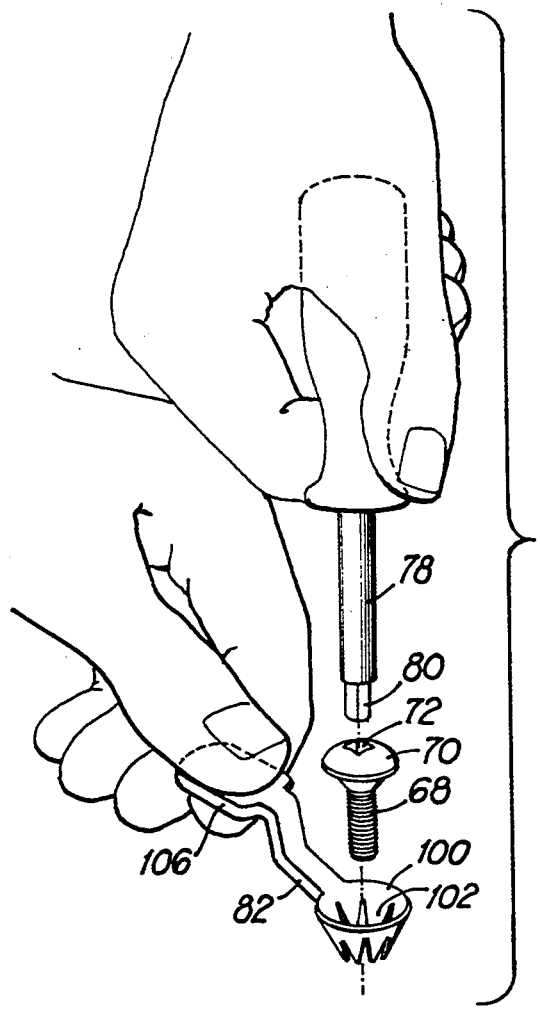
FIG 28
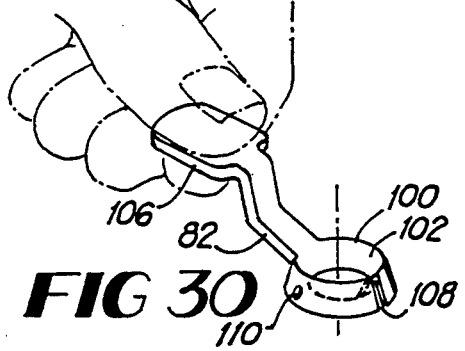
FIG 29
FIG 30

ANATOMICAL PRECONTOURED PLATING

This is a continuation of U.S. Ser. No. 07/518,221 filed May 3, 1990, U.S. Pat. No. 4,966,599 for "Anatomical Precontoured Plating, Instruments and Methods," which is a continuation of U.S. Ser. No. 07/274,699 filed Nov. 15, 1988 for "Anatomical Precontoured Plating, Instruments and Methods," which is a continuation of U.S. Ser. No. 07/035,658 filed Apr. 7, 1987, both abandoned, for "Anatomical Precontoured Plating, Instruments and Methods," all of which documents list the same inventor, Richard A. Pollock of Atlanta, Ga.

This invention relates to three-dimensionally shaped osteosynthesis plates for alignment and stabilization of fractured bones. Other aspects of the invention include fasteners and instruments for securing the plates to the skeleton and devices and methods for packaging, transporting and installing the plates and fasteners.

BACKGROUND OF THE INVENTION

Repair of dislocated bone involves two primary steps: realignment of the dislocated fragments or segments and stabilization of the bone. Dressings such as plaster or oil-soaked linen and wire have been used since antiquity for bone stabilization, but wire emerged as the prevalent appliance for bone stabilization in the nineteenth century.

Placement of wire loops through holes drilled in bone has long been an accepted technique, but more recent experience, during and after World War II, suggested that bone repaired with wire loops is not rigidly stable. The advent of mechanization and concomitant faster travel resulted in high velocity injuries more severe in nature than those previously encountered. Experience in treatment of such injuries has made it evident that bone fragments connected by wire loops are free to hinge along the fracture line. This bone fragment mobility interferes with healing and results in delayed recovery, skeletal deformity including midfacial shortening, and high rates of infection. Patients with complex injuries have often been crippled or disfigured for life, and many such injuries have been fatal.

Crude metal plates were introduced in Europe in approximately 1957 for the repair of orthopedic fractures. These plates, which were secured to bone with screws, advantageously prevented the bone fragment mobility that is often associated with wire-stabilized injuries. Subsequent generations of plates and fasteners, together with new instruments, allowed rigid stabilization of orthopedic and craniofacial fractures to become a reality. Complex, comminuted and severely dislocated fractures could then be effectively treated.

Typical of plates presently provided for cranial and facial osteosynthesis include those of the Wurzburg, Steinhauser and Champy systems sold in the United States by Walter Lorenz Surgical Instruments, Inc., Jacksonville, Fla., plates of Synthes, Inc., Basel, Switzerland and Paoli, Pa., and compression plates provided by Howmedica International, Inc., Kiel, Federal Republic of Germany. These plates present common, severe disadvantages, however.

Such plates typically comprise small, generally flat, elongated sections of metal. The sections contain round and perhaps elongated screw holes at various points along their lengths for fastening the sections to bone. The sections may be linear, curved, T-shaped, L-shaped or otherwise angled in their generally planar dimensions for positioning on various portions of the skeleton.

Because no surface of the human skeleton is flat, existing plates must be extensively twisted, formed and bent during surgery to conform to portions of the skeleton on which they are to be affixed. During a six to eight hour surgical procedure, as much as 30 to 45 minutes of time may be expended shaping and re-shaping metal plates. This additional time increases anesthesia requirements and operating room time and increases the potential of infection.

The inevitable over-bending and under-bending of plates during efforts to form the plates during surgery creates crimps and other surface imperfections in the plates and it alters their structural integrity due to metal fatigue. Surface imperfections can also irritate overlying tissue. Weakened structure due to excessive bending and twisting in the operating room is of paramount importance because it can lead to structural failure later; these plates frequently must remain in patients' faces for the rest of their lives and must undergo tremendous stresses, as for instance in the mandibular or ramus areas.

The heads of screws provided with present plates extend beyond the plane of the outer surfaces of the plates and create voids between bone and the periosteal lining. The contour of screw heads and often the plates are frequently transmitted through overlying soft tissue and thereby made visible on the patient's face; both screw heads and plates therefore frequently may be palpated beneath the skin's surface.

The planar nature of conventional plates increases this problem of transmission through the facial soft tissue. Rather than having edges which conform to and grip the bone, the edges of present plates frequently form a tangent with respect to the skeleton so that the patient may actually be able to push subcutaneous tissue between the plate edge and bone with his or her fingernail.

Known packaging techniques present additional difficulties. Plates and screws are presently provided on pegs or in slots together with installation tools in perforated metal boxes. They are arranged in various sizes, shapes and lengths and cannot be easily identified by name, so the surgeon finds it difficult to tell the nurse which plate will be used next. The plates and screws packaged in these metal boxes also require sterilization in an autoclave or other apparatus, so that addition valuable time prior to or during surgery is lost.

Conventional plates, screws and instruments are held in place by gravity in their metal boxes. If such a box is inverted while closed, the plates, screws and instruments become scrambled in the box. If the box is open while it is inverted or dropped, the plates, screws and instruments are scattered about the operational setting.

Screws must be delivered from the scrub nurse's station or table to the surgeon by means which allow them to be quickly and easily used. Present techniques include Phillips or cruciform head screwdrivers with clutches that grab the screwhead. The clutch sleeve is retracted once the screw is started into the bone. Such clutches are difficult to engage and disengage from screwheads, particularly after repeated use, because of rust in the clutch mechanism. The additional force required to disengage the clutch may jar delicate bone such as, for example, the bone of the inferior orbital rim. On the other hand, Phillips, slotted or cruciform screwdrivers without a clutch can disengage from the screwhead and interrupt insertion of the screw, alter the torque axis or alter screw penetration direction if the screw is self-tapping. Many existing screw designs also result in inadvertent disengagement or slippage of the screwdriver from the head. Existing slotted, cruciform or hexagonal-type screwheads all allow this disengagement.

SUMMARY OF THE INVENTION

The present invention provides plates, screws, instruments and methods which have been found to overcome these deficiencies. The invention takes advantage of the surprising fact that human adult craniofacial osseous structure and shape are highly similar among the population. Accordingly, plates can be preformed during manufacture to fit a large proportion of the human adult population. Consequently, less time is required during surgery to twist and bend the plates, and their structural characteristics need not be adversely affected by extensive bending, twisting and shaping. Furthermore, they can be made of harder and stiffer material and thus perform more effectively, since they do not need to be soft enough to allow the surgeon to bend and twist them easily in the operating room.

The plates may be packaged and presented for use on forms which simulate portions of the skull, so that their intended cranial or facial position is more easily recognized by members of the surgical team. Because bone thickness at particular craniofacial skeletal locations is highly consistent in the adult population, appropriate length screws may be packaged with the plates with which they are to be used, as for instance, by insertion through or adjacent to the plates on the skull-like packaging platform. Important surgical time is thus saved in selecting screws.

Screws for use with the present invention may have square-shaped recesses in order to prevent stripping and inadvertent disengagement from the screwdriver. Square recessed heads allow for greater longitudinal control of the screws as they are started and for application of greater selected torque without disengagement of the screwdriver or failure of the screwdriver seat in the screwhead.

A first screw transport unit for transporting a screw from its packaging to the surgical field and for starting the screw in the bone has a recessed clutch that is precisely sized to receive the head of the screw. The screw starter features a square protrusion that matches the square recess of the screwhead and that is designed to absorb the torque necessary to start the screw into the bone. The screw starter is then removed and final tightening of the screw is completed with the square tipped screwdriver. A second transport system is a breakaway hub in which the screw can be dispensed. The hub has a clutch which is designed to capture precisely the head of the screwdriver. The screw is transported by the hub to the surgical field and started into the bone. The hub may contain a fault which fails upon application of a predetermined torque level or pressure so that the hub breaks away and can be removed with a tab or other means for easy retrieval. A radiographic marker may also be included in the hub.

Supplemental screws may be dispensed from a round compartmentalized container with a rotatable cover. A single opening allows access to a compartment which may contain one or more sterile screws of designated length and diameter. The screws may be contained in sealed, presterilized packaging. Supplemental plates may be dispensed from similar dispensers.

It is thus an object of the present invention to provide bone stabilization plates that are shaped in three dimensions during manufacturing to require less bending and contouring during surgery in order to save time, minimize surface irregularities in the installed plates and reduce metal fatigue due to bending and twisting.

It is an additional object of the present invention to provide bone stabilization plates that are arced in cross-section with respect to their longitudinal axes in order better to grip bone and minimize space between plate and bone.

It is an additional object of the present invention to provide bone stabilization plates that transmit fewer and smaller surface irregularities through the soft tissues of the patient's face.

It is a further object of the present invention to provide bone stabilization plates and groups of such plates which may be packaged mounted on forms resembling the portion of the craniofacial skeleton to which they will be attached, in order to allow all members of the surgical team more easily to recognize and refer to various plates and their intended position in use.

It is a further object of the present invention to provide bone stabilization place fasteners whose heads have square recesses in order to minimize inadvertent disengagement of the screws from screwdrivers and to absorb greater torque with less chance of screw head failure.

It is a further object of the present invention to provide bone stabilization place fasteners which are packaged with the plates mounted on forms resembling the portion of the craniofacial skeleton to which they will be attached, in order to minimize time necessary for screw selection and to allow for ease of reference by members of the surgical team.

It is a further object of the present invention to provide screw starters and transporters which allow screws to be more easily transported to the surgical field and which minimize potential for screw loss or improper starting into the bone.

It is a further object of the present invention to provide screw and plate dispensers which allow presterilized screws and plates to be dispensed easily and quickly and which facilitate accounting for screws and plates utilized during the operation.

It is a further object of the present invention to provide instruments for more efficient and effective application, stabilization and contouring of bone stabilization plates.

Other objects, features and advantages of the present invention will become apparent with reference to the remainder of the disclosure, claims and drawings.

BRIEF DESCRIPTION OF THE DRAWINGS

FIG. 11A is a front elevational view of a glabellar plate according to the present invention.

FIG. 11B is a plan view of the plate of FIG. 11A.

FIG. 12A is a front elevational view of a medial canthal plate according to the present invention.

FIG. 12B is a right side elevational view of the plate of FIG. 12A.

FIG. 13 is a front elevational view of a nasofrontal plate according to the present invention.

FIG. 14A is a front elevational view of a lateral buttress plate according to the present invention.

FIG. 14B is a plan view of the plate of FIG. 14A.

FIG. 22 is a perspective view of a first type of fastener according to the present invention.

FIG. 23 is a cross-sectional view of the fastener of FIG. 22.

FIG. 24 is a perspective view of a second type of fastener according to present invention.

FIG. 25 is a perspective view of a third type of fastener according to the present invention.

FIG. 26 is a cross-sectional view of the fastener of FIG. 25.

FIG. 27 is a perspective view of a fourth type of fastener according to the present invention.

FIG. 28 shows a first type of screw starter and a screwdriver according to the present invention.

FIG. 29 shows a second type of screw starter according to the present invention.

FIG. 30 shows a third type of screw starter according to present invention.

DETAILED DESCRIPTION OF THE DRAWINGS

Figure 1:
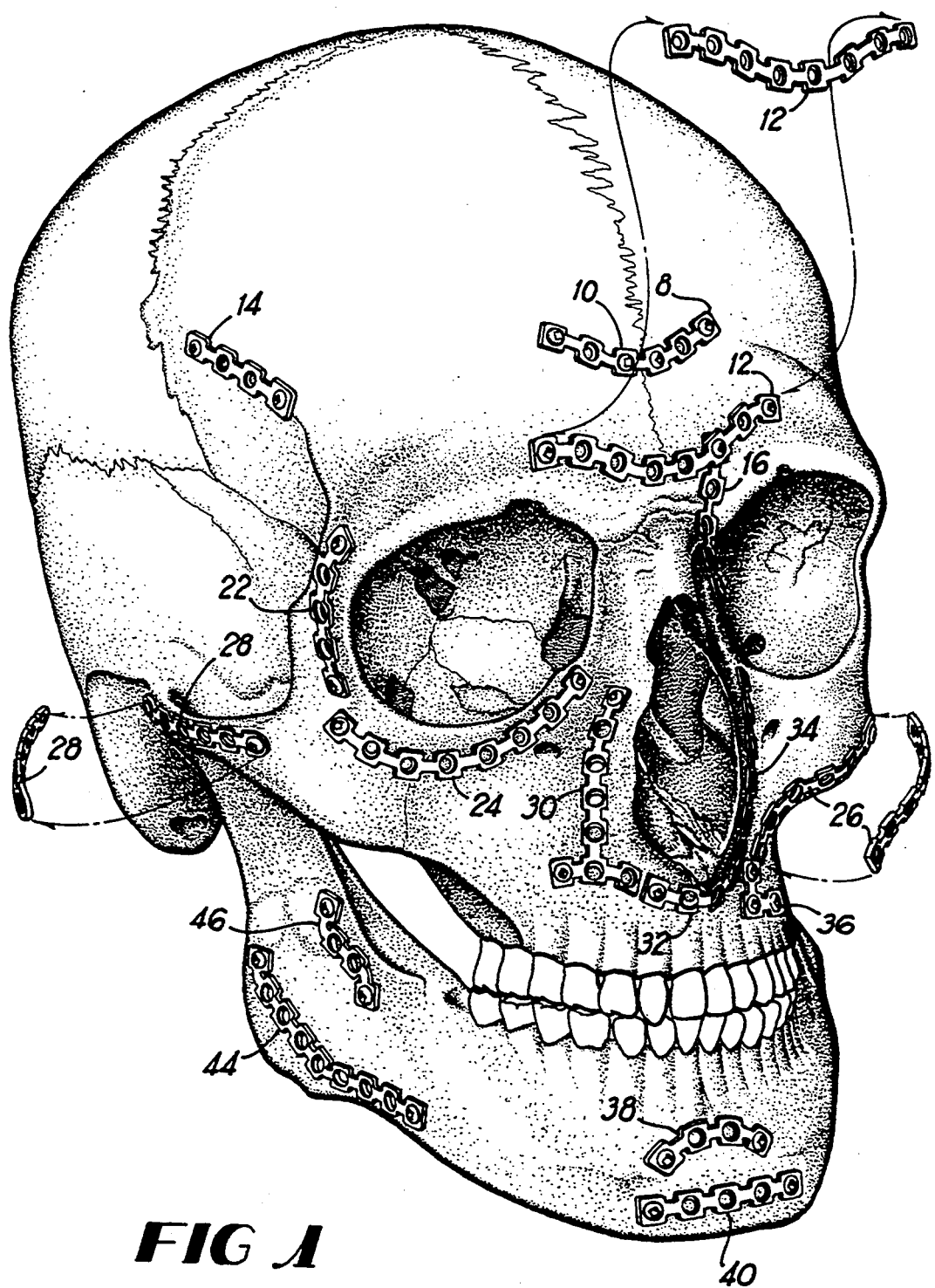
FIG. 1 is a perspective view of the craniofacial structure showing installed bone stabilization plates according to the present invention.
Figure 2:
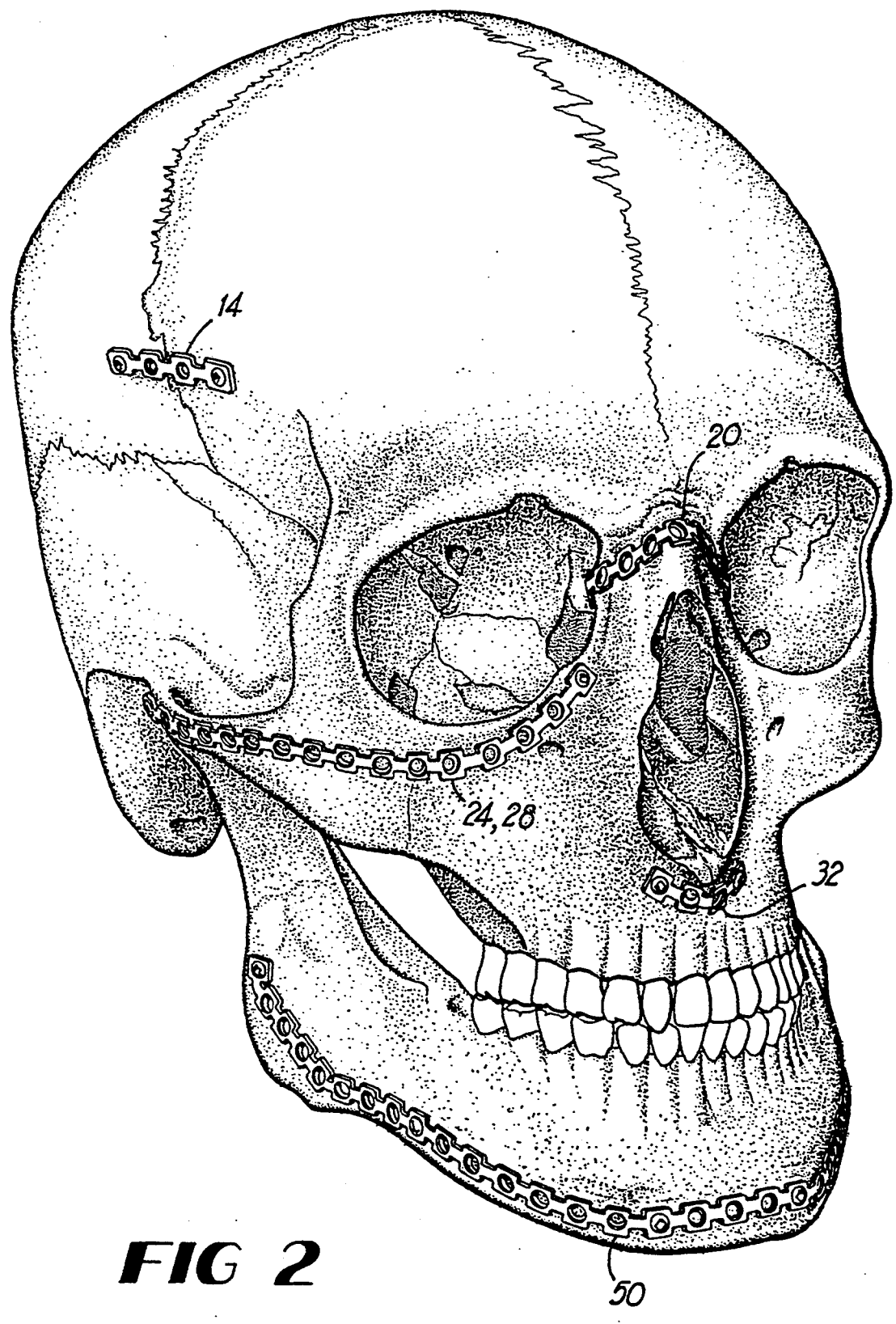
FIG. 2 is a perspective view of the craniofacial structure showing additional installed bone stabilization plates according to the present invention.
Figure 3:
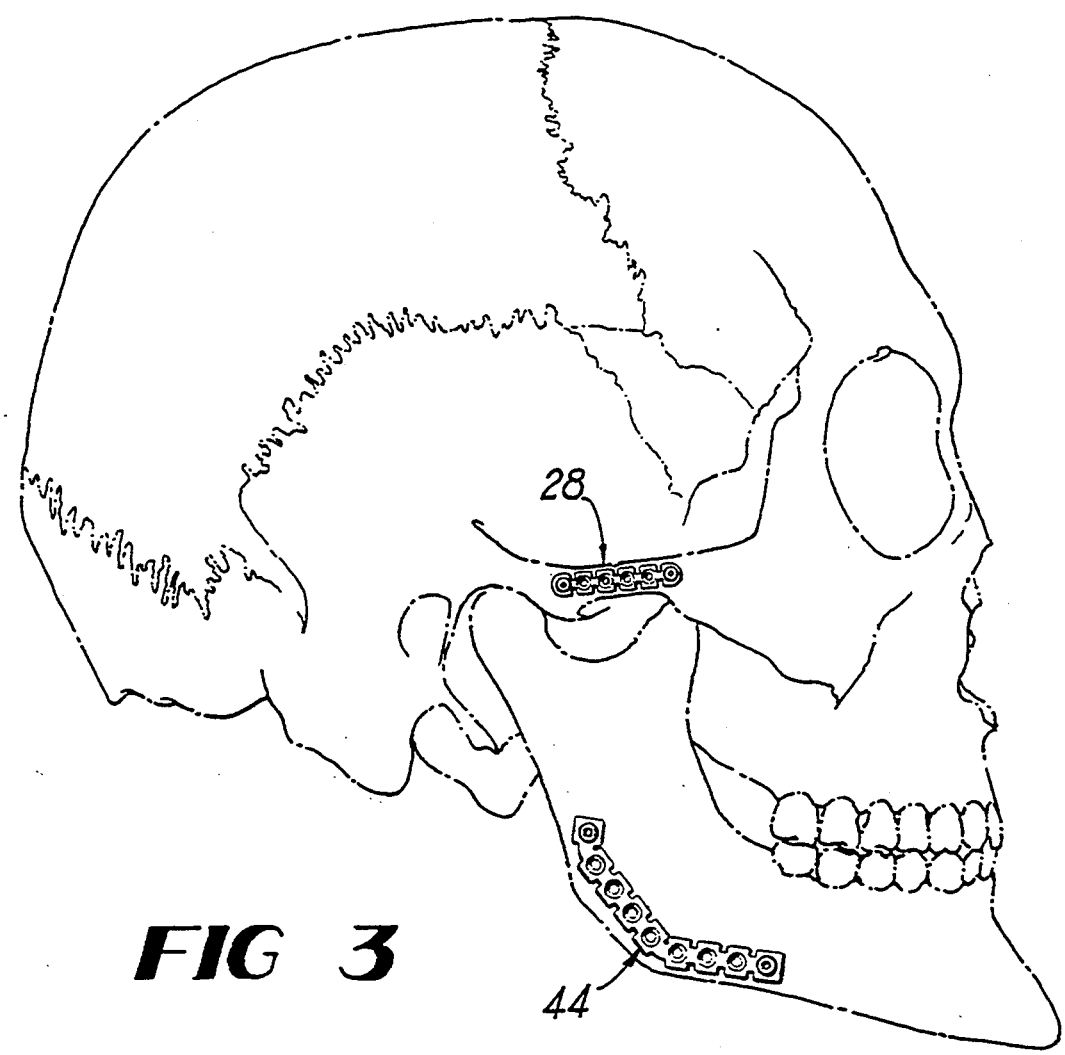
FIG. 3 is a side elevational view of craniofacial structure showing other installed bone stabilization plates according to the present invention.

FIGS. 1-3 illustrate configuration and placement of various osteosynthesis or bone stabilization plates 8 according to the present invention. The plates shown in these figures can be generally categorized as falling in the frontal or frontonasal, zygomatic, maxillary and mandibular groups.

The frontal group contains upper forehead plate 10, glabellar plate 12, panskull plate 14, nasofrontal suspension plate 16, utility plate 18 (not shown) and medial canthal reconstruction plate 20 shown in FIG. 2. The zygomatic group contains frontozygomatic suture plate 22, inferior orbital rim plate 24, lateral buttress plate 26 and zygomatic arch plate 28. The maxillary group contains medial buttress "T" 30, lateral buttress 26, inferior orbital rim (abbreviated) plate 24 (not shown); split palate plate 32, medial buttress "J" plate 34 and "L" plate 36. The mandibular group contains upper symphysis plate 38, marginal symphysis plate 40 (not shown), interior body plate 42, angle plate 44, ridge plate 46, posterior body plate 48 (not shown) and hemimandible plate 50 shown in FIG. 2. These plates are manufactured according to the present invention to be precontoured and secured to locations on the craniofacial skeleton corresponding with their names as generally shown in FIGS. 1-3.

Plates 8 according to the present invention, unlike earlier plates, are manufactured to correspond in three dimensions to their locations on the craniofacial skeleton. An example is lateral buttress plate 26 shown in FIGS. 1 and 13. Unlike earlier osteosynthesis plates, this plate is shaped during manufacture in the form of an "S" in its flat dimension. This dimension is referred to as the "face dimension 52." The plate is arched in the cross-sectional dimension perpendicular to the fact dimension to form a convex top face 51 and a concave bottom face 53. This second dimension is referred to as the "cross-sectional dimension 54." Also unlike previous plates, the plate is shaped during manufacture in the third dimension to contour to the portion of the bone to which it will be attached. This third dimension, which is perpendicular to the face dimension 52 and the cross-sectional dimension 54, is referred to as the "contour dimension 56."

Figure 10:
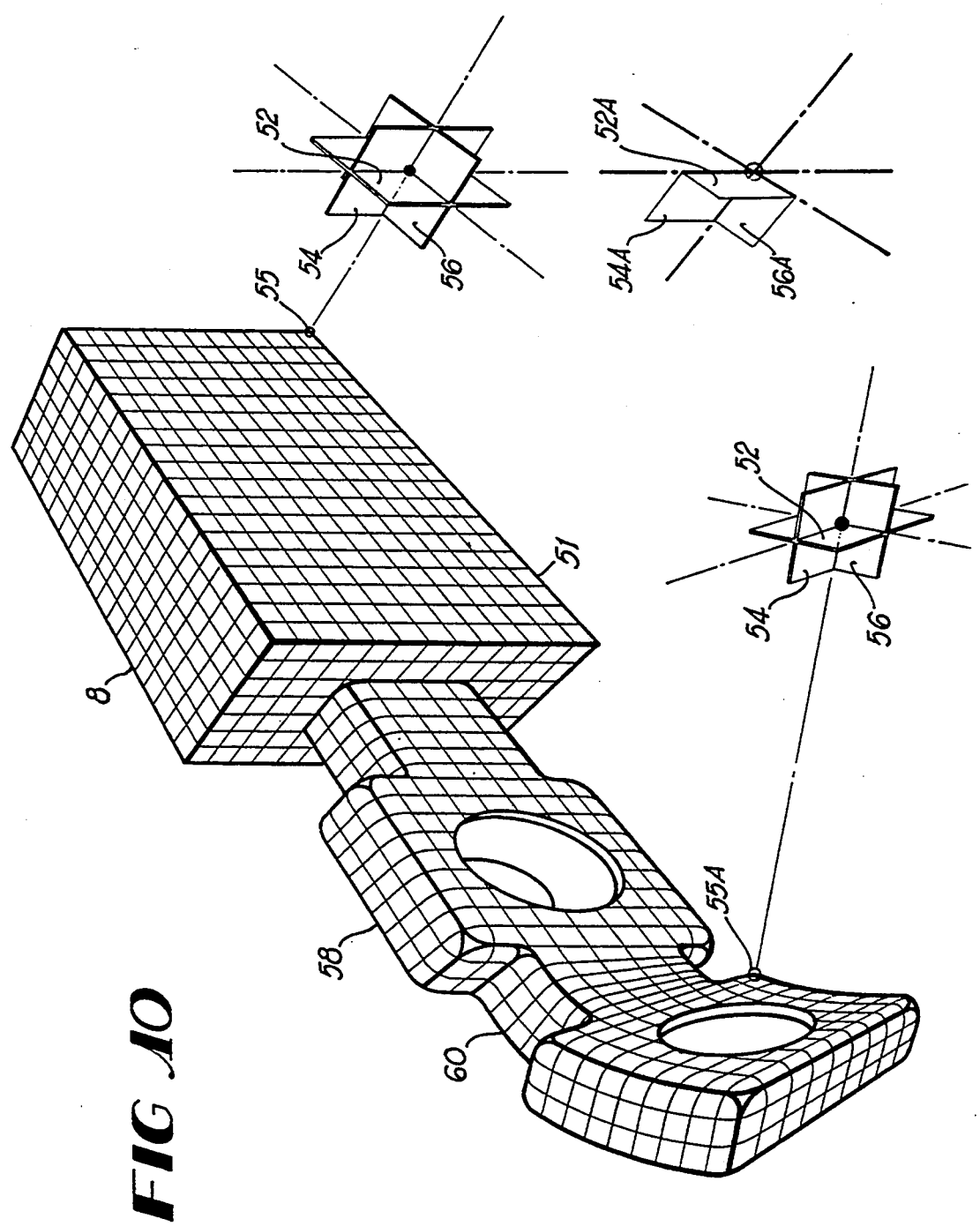
FIG. 10 is a perspective view of a plate according to the present invention showing absolute and relative reference systems used in connection with the plates.

Face dimension 52, cross-sectional dimension 54 and contour dimension 56 are illustrated in FIG. 10 which shows diagrammatically a portion of a plate 8 according to the present invention formed from a hypothetical block of material. These dimensions correspond to the orientation of particular points on or within plate 8. Thus, face dimension 52 with respect to reference point 55 or 55A on top surface 51 of plate 8 is the plane which is tangent to top surface 51 at that point. Cross-sectional dimension 54 is the plane which contains point 55 or 55A, which is orthogonal to face dimension 52 and which contains the cross section of plate 89 at that point. Contour dimension 56 is the plane which is orthogonal to face dimension 52 and cross-sectional dimension 54 at reference point 55 or 55A.

If plate 8 were flat and straight, as are many conventional plates, then face dimension 52, cross-sectional dimension 54 and contour dimension 56 would correspond to face plane 52A, cross-sectional plane 54A and contour plane 56A as shown in FIG. 10. In such a case, face plane 52A would be tangent to all points on top surface 51, and all cross-sectional dimensions 54 of plate 8 would be orthogonal to top surface 51 and face plane 52A. Face dimension 52 and face plane 52A; cross-sectional dimension 54 and cross-sectional plane 54A and contour dimension 56 and contour plane 56A would therefore be coincident. Plane 52A, 54A and 56A thus define an absolute reference system while dimensions 52, 54, and 56 define a reference system that is relative with respect to locations on plates 8.

A plate 8 according to the present invention which is cast can have a crystalline structure which remains aligned even though the plate is contoured in three dimensions. By contrast, a conventional plate which must be bent and twisted significantly in the operating room requires deformation of the alignment of the plate's crystal lattices according to the angular differences in three dimensions between relative dimensions 52, 54 and 56 at any point in the plate and absolute planes 52A, 54A and 56A. Such deformation can cause weakness due simply to mechanical alterations in the crystalline structure and due to other effects such as frictional heat generated during bending and twisting. These can adversely affect hardness, stiffness and tensile strength. The present invention can thus minimize weaknesses in the structure of plates 8 which would otherwise be caused by excessive bending, twisting and contouring in the operating room.

Plates 8 can be made of stainless steel, titanium, vitallium (an alloy of cobalt, chromium and molybdenum) or other suitable, even non-metallic, materials. Stainless steel is subject to corrosion which exposed to electrolytes containing hydrogen and oxygen, so installed stainless steel plates may corrode over time and cause localized metallosis. Stainless steel is also subject to contact and friction, or fretting, corrosion. Stainless steel plates with protective coating highly polished surfaces can have better corrosion characteristics, but the surgical team must exercise great care not to damage this surface and affect corrosion potential.

Titanium is a softer metal than stainless steel and is frequently found not to be sufficiently rigid to withstand large forces placed on bone stabilization plates, particularly in the mandibular area. Vitallium is desireable because it can remain in the body for long periods of time without metallosis and need for removal, because it resists fretting, corrosion and oxidation, and because it is a particularly hard alloy.

Plates 8, because they are precontoured and require minimal bending and twisting in the operating room, are particularly well-suited to be made of polymeric, composite or other non-metallic materials which are not as easily shaped at room temperature as are metals. Plates 8 of such materials may also be manufactured to be resorbable in the body; such plates gradually wear away so that any irregularities transmitted through the patients' facial soft tissues diminish over time. Such resorbable materials include, for instance, compounds of polyglycolic acid.

Plates 8 are preferably cast, but they may be stamped, forged, cut, machined or formed by any other suitable or appropriate method. They may be shaped in the contour dimension 56 during casting, initial stamping or forging, or they may be shaped in a subsequent manufacturing step. After a plate 8 has been shaped or while it is being shaped as desired in all three dimensions, it may be subjected to a hardening or tempering process such as cycles of heating and quenching.

Figure 15:
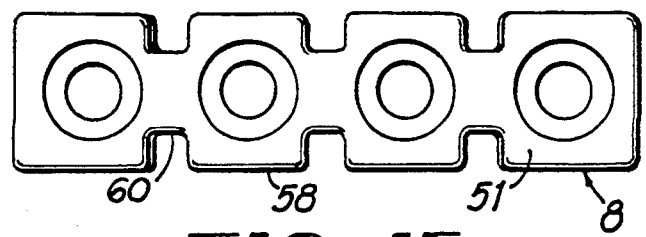
FIG. 15 is a face plane view of a plate of the present invention having a rectangular configuration for plate segments.
Figure 16:
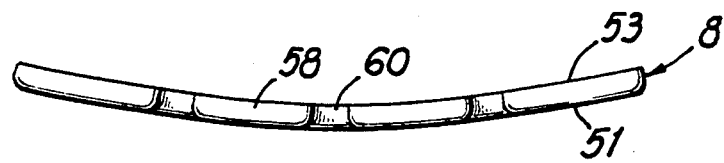
FIG. 16 is a contour plane elevational view of the plate of FIG. 15.
Figure 17:
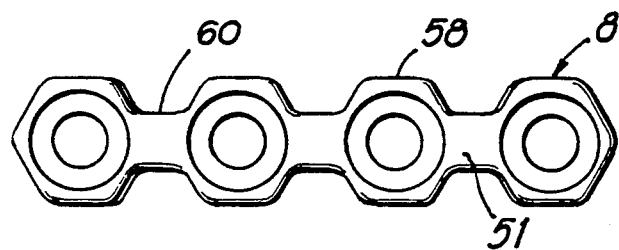
FIG. 17 is a face plane elevational view of a plate of the present invention having a second, hexagonal shaped segment configuration.
Figure 18:
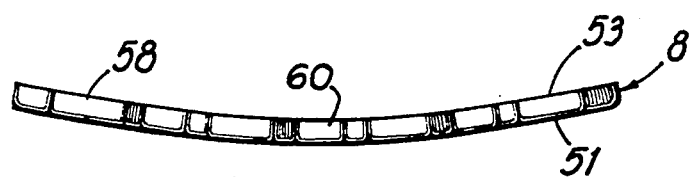
FIG. 18 is a contour plane elevational view of the plate of FIG. 17.
Figure 19:
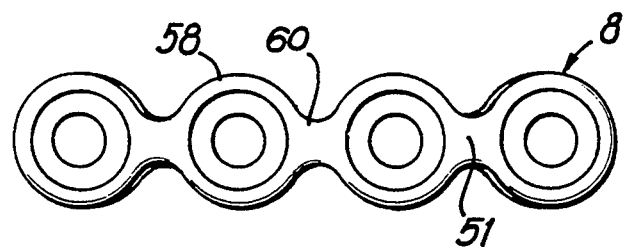
FIG. 19 is a face plane elevational view of a plate of the present invention with a third, generally circular shaped segment configuration.
Figure 20:
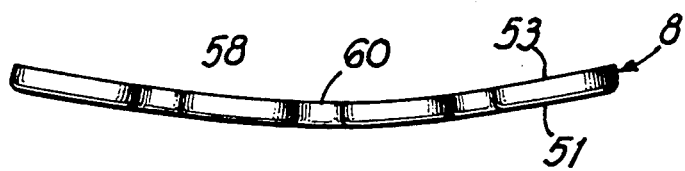
FIG. 20 is a contour plane elevational view of the plate of FIG. 19.

Plates 8 can, but need not, comprise a series of segments 58 connected by throat sections 60. Segments 58 may be generally rectangular as shown in FIGS. 15 and 16, generally hexagonal as shown in FIGS. 19 and 20 or of any other desired shape. Alternatively, plates 8 can exclude throat sections 60 so that their sides in the face dimension are continuous, as, for instance, linear, curvilinear or curved.

A plate 8 according to the present invention may be designed so that its cross-sectional moment of inertia or polar moment of inertia is constant. Such a plate has curved sides in its face dimension 52. Those curves, together with the screw hole definitions and the shape of the plate in the cross-sectional dimension, can be configured to provide a uniform polar moment of inertia in the cross-sectional dimension for uniform torsional resistance about the longitudinal axis, or a uniform moment of inertia in the cross-sectional dimension for uniform resistance to bending in the contour dimension. Plates 8 may also be constructed which satisfy both of these conditions for uniform twisting and bending in the contour dimension, and they may also have uniform moments of inertia in the contour or face dimensions for uniform resistance to bending or twisting or both. Such designs allow the plates to bend more predictably and thus be finally shaped in surgery more easily and quickly. Such moments of inertia may be calculated graphically, using incremental techniques or be any other appropriate method.

Figure 4:
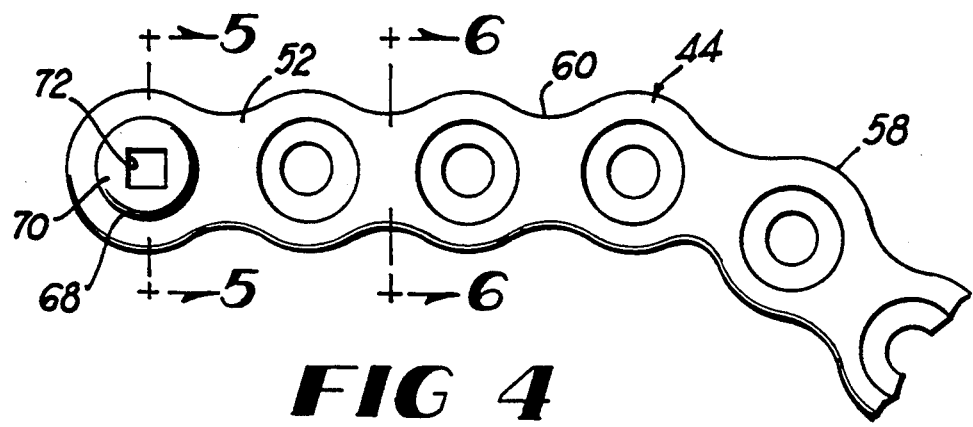
FIG. 4 is a plan view of a portion of the mandibular angle plate shown in FIG. 3.
Figure 5:
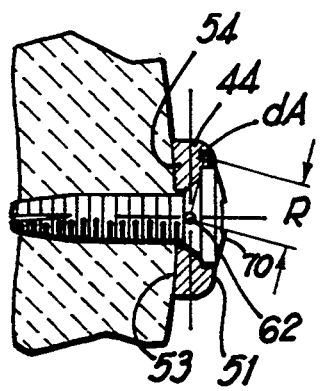
FIG. 5 is a cross-sectional view of the plate of FIG. 4 taken along section 5—5 of that plate.
Figure 6:
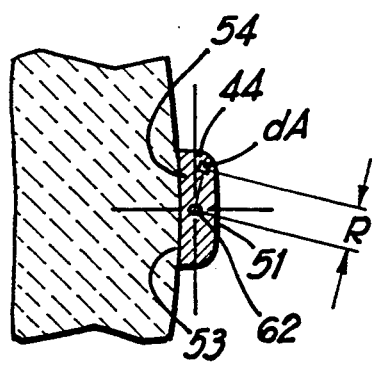
FIG. 6 is a cross-sectional view of the plate of FIG. 4 taken along sections 6—6 of that plate.

FIGS. 4, 5 and 6 illustrate a plate 8 according to the present invention with a uniform polar moment of inertia in the cross-sectional dimension 54. FIG. 6 schematically shows the concept of determining the polar moment of inertia, which is the integral of the product of each incremental area dA of the cross section multiplied by the square of its distance R from the center of gravity of the cross section. Because more area is located farther from the center of gravity in a cross section containing a screw hold S as shown, for example, in FIG. 5, the throat 60 cross sectional area as shown in FIG. 6 is larger than the segment 58 cross sectional area.

Figure 7:
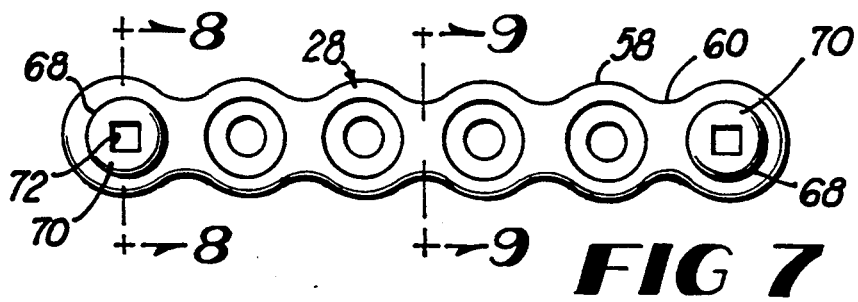
FIG. 7 is a plan view of the zygomatic arch plate shown in FIG. 3.
Figure 8:
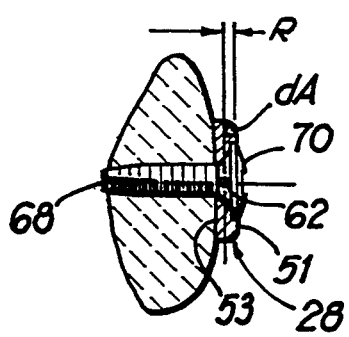
FIG. 8 is a cross-sectional view of the plate of FIG. 7 taken along section 8—8 of that plate.
Figure 9:
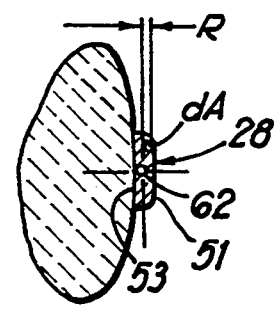
FIG. 9 is a cross-sectional view of the place of FIG. 7 taken along section 9—9 of that plate.

FIGS. 7, 8 and 9 demonstrate a plate design for uniform resistance to bending in the contour dimension. The moment of inertia about bending axis 66 as shown in FIGS. 8 and 9 is designed to be constant along longitudinal axis 62. This moment is defined as the integral of the product of incremental area dA of the cross section multiplied by the square of their distance R from the axis 66.

FIGS. 11A and 11B show a front elevational and a plan view, respectively, of a glabellar plate 12 manufactured according to the present invention. The plate is configured in the face plane 52 to be generally U-shaped. It is also configured in the contour dimension 56 and the cross-sectional dimension 54 to conform to the skeleton. The contour dimension 56 configuration and the cross-sectional 54 dimension twist are also shown in FIG. 11B, the plan view of glabellar plate 12. FIGS. 11A and 11B demonstrate the subtlety and complexity of the curves required in the glabellar plate 12 to conform to the glabella.

FIGS. 12A and 12B show the more radically configured medial canthal plate 20, while FIG. 13 shows the nasofrontal separation plate 16. The lateral buttress plate 26, which is also radically configured, is shown in FIGS. 14A and 14B. These figures demonstrate the advantages to be gained by preconfiguring bone stabilization plates 8; curves in the plate are more continuous to reduce facial distortion in the patient, time is saved in the operating room, and the plates are subjected to far less metal fatigue and crimping because they need to be bent and twisted less in the operating room than previous plates. Plates 8 can also be made of harder and stiffer material because they require less bending in the operating room.

FIGS. 15–20 show various face plane configurations for segments 58 and throat sections 60 of plates 8.

FIGS. 22–27 show fasteners or screws 68 according to the present invention to secure plates 8 to the craniofacial skeleton. Screws 68 are preferably made of the same material as plates 8 to reduce electrolysis and galvanic erosion between plates 8 and screws 68 and consequently corrosion while plates 8 are in the patient. Screws 68 may be self-tapping as shown in FIGS. 22, 23, 25 and 26 or machine threaded as shown in FIGS. 24 and 27. Screws 68 may have convex or flat heads as shown in FIGS. 22–24 and 25–27 respectively. Significantly, screws 68 according to the present invention having heads with square recesses 72 have been shown to be advantageous in several respects. Square recess 72 minimizes inadvertent slippage or failure of the screwdriver-screw connection as screw 68 is torqued into the bone. Similarly, square recess 72 allows the screwdriver to remain aligned with the screw axis as torque is applied and thus helps to minimize misalignment of the screw in the skeleton.

Figure 21:
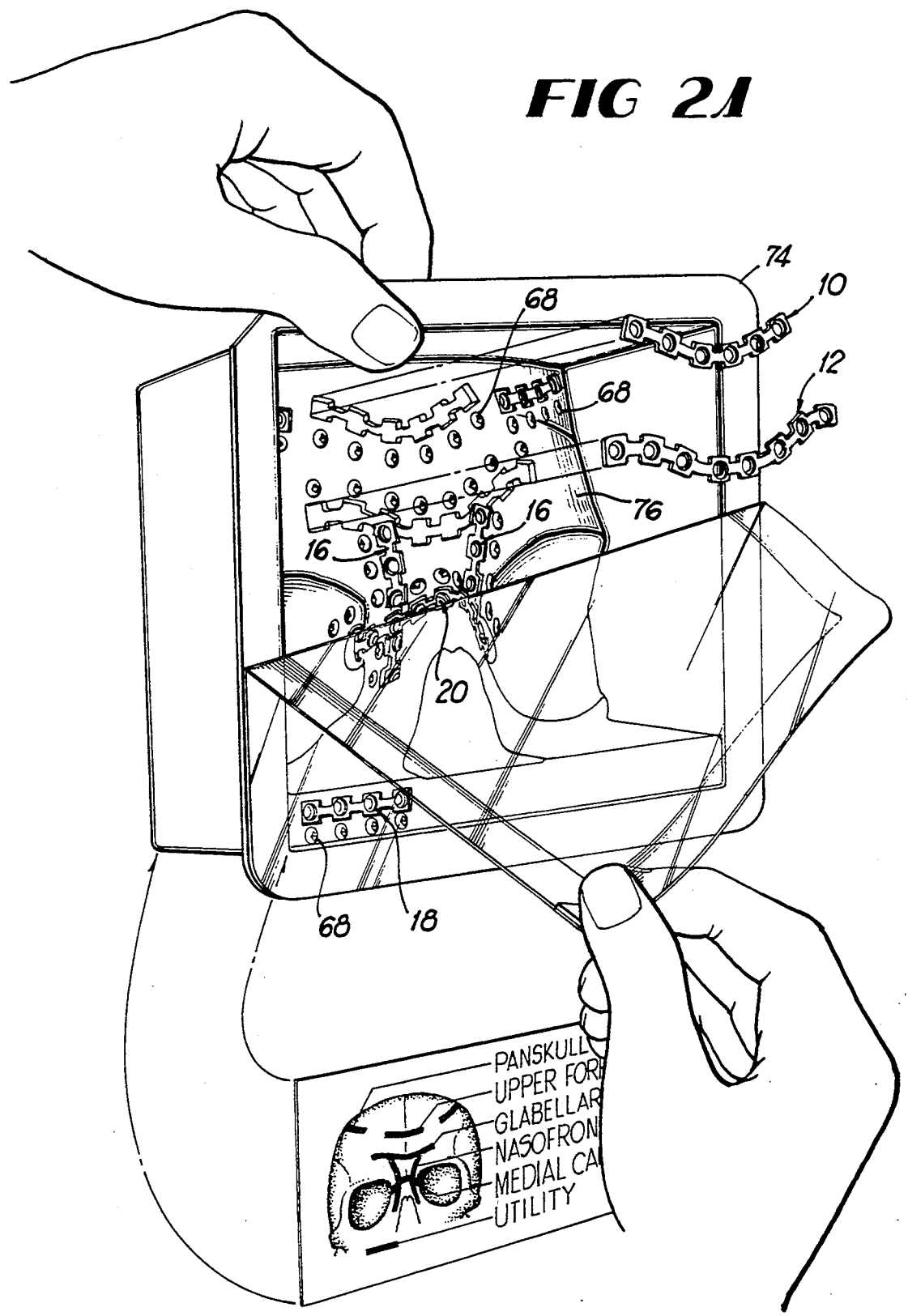
FIG. 21 is a perspective view of packaging for storing, transporting and presenting plates according to the present invention.

Plates 8 and screws 68 may be packaged as shown in FIG. 21 in a manner to allow all members of the surgical team easily to identify and refer to appropriate plates 8 and the screws 68 by which each plate 8 should be secured to the skeleton. They may also, of course, be packaged separately in individual packages. Packaging 74 contains a presentation face 76 to which plates 8 and screws 68 are secured. The packaging shown in FIG. 21 is for a frontal sinus with nasofrontal separation case. It comprises upper forehead plate 10, glabellar plate 12, panskull plate 14, nasofrontal suspension plate 16, a utility plate 18 and a medial canthal plate 20. These are placed on the presentation face 76, which resembles a human face, at the locations corresponding to the skeletal sites to which they should be installed. Screws 68 can be inserted through holes in each plate 8 or inserted in presentation face 76 near their intended location in plates 8. Plates 8 which must be attached to thicker bones can thus be packaged on presentation face 76 with longer screws 68 while plates 8 which will be attached to thinner bone can be packaged with shorter screws 68. Additional screws 68 may be mounted on presentation face 76 near to screws they supplement.

Plates 8 and screws 68 can be advantageously packaged in fourteen sets which correspond to fourteen groupings of craniofacial trauma and repair. These sets are presented in the following table:

I. Frontal Sinus Fracture
  A. Upper forehead 10
  B. Glabellar 12
  C. Two panskull 14
  D. Utility plate 18
II. Frontal Sinus with Nasofrontal Separation
  A. Upper forehead 10
  B. Glabellar 12
  C. Two panskull 14
  D. Nasofrontal suspension 16
  E. Utility 18
  F. Medial canthal "C" reconstruction 20
III. Zygomatic, Right
  A. Frontalzygomatic suture 22
  B. Inferior orbital rim 24
  C. Lateral buttress 26
IV. Zygomatic, Left
  A. Frontozygomatic suture 22
  B. Inferior orbital rim 24
  C. Lateral buttress 26
V. Zygomatic, Complex, Right
  A. Frontozygomatic suture 22
  B. Inferior orbital rim 24
  C. Lateral buttress 26
  D. Zygomatic arch 28
VI. Zygomatic, Complex, Left
  A. Frontozygomatic suture 22
  B. Inferior orbital rim 24
  C. Lateral buttress 26
  D. Zygomatic arch 28
VI. Maxillary, Lefort I or II
  A. Right medial buttress "T" 30
  B. Left medial buttress "T" 30
  C. Right lateral buttress 26
  D. Left lateral buttress 26
  E. Right inferior orbital rim 24 (abbreviated)
  F. Left inferior orbital rim 24 (abbreviated)
VII. Maxillary with Split Palate
  A. Split palate 32
  B. Right medial buttress "T" 30
  C. Left medial buttress "T" 30
  D. Right lateral buttress 26
  E. Left lateral buttress 26
  F. Right inferior orbital rim 24 (abbreviated)
  G. Left inferior orbital rim 24 (abbreviated)
IX. Mandibular Symphysis/Body, Right
  A. Upper symphysis 38
  B. Marginal symphysis 40
  C. Anterior body 42
X. Mandibular Symphysis/Body, Left
  A. Upper symphysis 38
  B. Marginal symphysis 40
  C. Anterior body 42
XI. Mandibular Angle/Body, Right
  A. Angle 44
  B. Ridge 46
  C. Posterior body 48
XII. Mandibular Angle/Body, Left
  A. Angle 44
  B. Ridge 46
  C. Posterior body 48
XIII. Mandibular, Comminuted/Complex, Right
  A. Hemimandible 50, spanning ramus to contralateral parasymphysis
XIV. Mandibular, Comminuted/Complex, Left
  A. Hemimandible 50, spanning ramus to contralateral parasymphysis These packages represent the "lowest common denominators" of plates needed for typical injuries to the craniofacial skeleton. Other plates may be developed and other sets may be used. Many cases will require more than one package of plates. An auto accident victim with complex injuries in the sinus, orbital rim and ramus areas, for instance, may require frontal sinus, zygomatic and mandibular angle/body packages.

The fourteen types of packages can be more easily accounted for than the many types of plates 8 they contain. Plates 8 according to the present invention can thus more easily be ordered, stocked, obtained by the surgeon and charged to the patient's account. The packages may be presterilized so that valuable anesthesia time is not lost while the surgeon is waiting for plates 8 or screws 68 to be sterilized. This may be accomplished, for instance, by sealed presterilized packaging 74 with peel-back top whose contents may be sterilized during manufacture. Presentation face 76 may be of any convenient material such as polymeric foam, vacuum-formed plastic material or other appropriate materials. Plates 8 may also, of course, be packaged in conventional peel-back top packages, metallic boxes or other containers individually or in other groups.

Screwdriver 78, shown in FIG. 28, has a square protrusion 80 for cooperating with square recesses 72 in screws 68. The protrusion 80 penetrates deeply enough into recesses 72 to assure that the screwdriver torque axis is aligned with the screw axis in order to minimize misalignment of screw 68 in bone. The square configuration of protrusion 80 also reduces the likelihood that protrusion 80 will slip in or strip recesses 72 and screws 68, or that they will cause screwhead 70 to fail, as can happen with flathead or cruciform head screws.

Screw starters 82 according to the present invention can take the form of, among other things, a disposable or permanent unit 84 as shown in FIG. 29 used to transport screws 68 to the surgical field and start them into the bone, or collars 100 shown in FIGS. 28 and 30 which are used to transport screws 68 to the surgical field and align them with the bone to be penetrated.

Unit 84 may be cylindrically shaped with a shank 88 connected to a handle 90 and a head 92. Head 92 has a cavity 94 which captures screwheads 70 by friction, interference or other desired means. In the preferred embodiment, cavity 94 captures screwheads 70 by means of a frictional collar 96 within cavity 94. Collar 96 is of slightly smaller inner circumference than screwheads 70. Cavity 94 also has a square protrusion 98 which matches the square protrusion 80 on screwdriver 78 and thus which cooperates with square recesses 72 on screw 68. In use, a screw 68 is inserted head-first into cavity 94 so that protrusion 98 fits within recess 72 of the screw 68. Screw 68 may then be transported to the surgical field in unit 84 and started into the bone.

Alternatively, collar 100 illustrated in FIG. 30 may be utilized. Collar 100 is a truncated cylinder with a countersink 102 to receive the countersunk portion of head 70 of screw 68. The shank of screw 68 penetrates through the face 104 of collar 100 opposite the countersink 102. A tab 106 is attached to collar 100 for gripping it. Collar 100 may contain a fault as shown in FIG. 30 so that it fails when screw 68 is driven a certain distance into the bone or upon application of a predetermined pressure. Collar 100 can be equipped with a radiographic marker 110 for safety purposes. Screws 68 may be provided in packaging 74 already inserted through collars 100 so that screws 68 may be easily transported and started.

Figure 31:
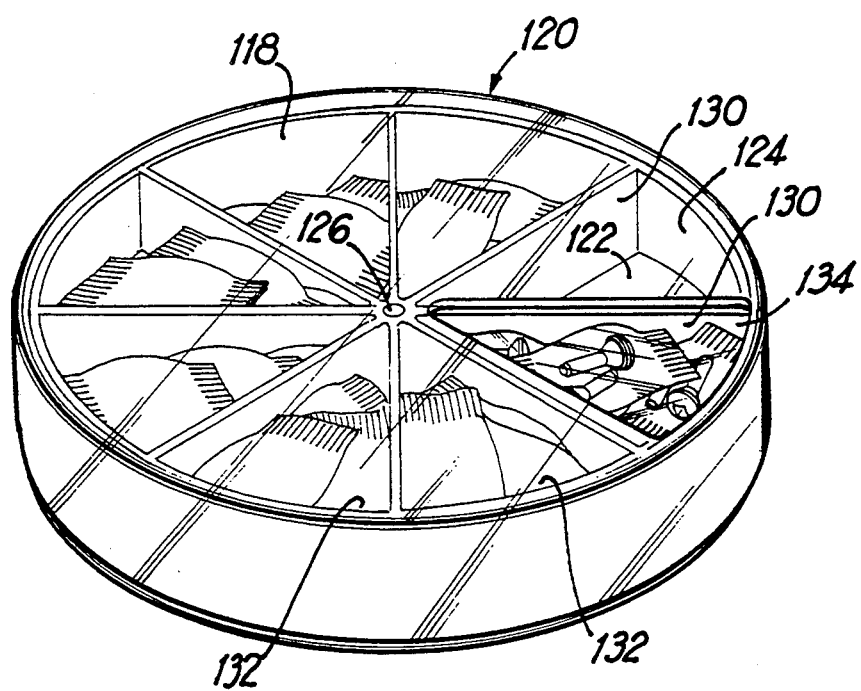
FIG. 31 shows a screw dispenser according to the present invention.

Screws 68 may also be dispensed from a dispenser 120. Dispenser 120 may take the form shown in FIG. 31 having a circular floor wall 122 connected to a cylindrical side wall 124. A pedestal 126 is connected to the center of the floor wall 122 and is rotatably attached to a circular cover 128. The dispenser 120 is divided into sections by a plurality of section walls 130 extending from the pedestal 126 to the side wall 124. Cover 128 has an opening 134 which corresponds in shape generally to a section 132. Cover 128 may thus be rotated to dispense various lengths of screws 68. Screws 68 may be packaged in presterilized plastic or other desirable packaging. Dispenser 120 may be mounted to an underlying surface with fasteners 136 such as screws or bolts. Similar dispensers 120 may be utilized for plates 8.

The parts, screws and instruments of the present invention allow for efficient and effective treatment. The surgeon evaluates the injury to determine which sets 74 of plates 8 are required. If the evaluation is inaccurate or incomplete, additional presterilized packages can be obtained immediately without the need to wait while additional plates are sterilized. The fracture is exposed and reduced. The surgeon determines which plates are to be applied, and the nurse easily understands which plates are needed because each plate 8 is situated in the packaging on presentation face 76 that resembles the portion of the skeleton on which the plate will be installed. Screws 68 packaged with the plates 8 are similarly easily identified.

The surgeon then performs any minor bending or crimping that may be required finally to tailor the contour of the plate to the skeleton to which it will be affixed. Screws 68 are then started using screwstarters 82 and finally driven using screwdriver 78. Screws 68 are then tightened to install the plate.

The foregoing is provided for illustration and description of the invention. Modifications and adaptations to the embodiments disclosed will be apparent to those of ordinary skill in the art and may be made without departing from the scope or spirit of the invention.

I claim:

1. A method of manufacturing an osteosynthesis plate having a top face and a bottom face, comprising the steps of:
   (a) selecting a craniofacial stabilization site on the human skull which is desired to be stabilized using an osteosynthesis plate;
   (b) preparing a stamp that has been contoured in three dimensions to fit the structure and shape of craniofacial sites on a plurality of human skulls whose locations on the skulls correspond to the location of the craniofacial stabilization site;
   (c) providing material for forming the plate; and
   (d) stamping the material to form an osteosynthesis plate that is contoured in three dimensions to fit the structure and shape of the craniofacial sites on the plurality of human skulls corresponding to the craniofacial stabilization site, by pressing the stamp against the entire top face and bottom face of the plate.

2. A method of manufacturing an osteosynthesis plate according to claim 1 further comprising the step of cutting the plate from the material, apart from the step of stamping the material.

3. A method of manufacturing an osteosynthesis plate according to claim 2 in which the step of cutting the plate from the material occurs before from the step of stamping the material.

4. An osteosynthesis plate manufactured according to the method of claim 1.

5. A method of manufacturing an osteosynthesis plate that has a top face, a bottom face and a plurality of holes connecting the top and bottom faces, and that is curved in the face dimension, cross sectional dimension and contour dimension to fit a site on the craniofacial portion of the human skull that is desired to be stabilized by virtue of having been curved in those dimensions to fit the structure and shape of craniofacial sites on a plurality of human skulls whose locations on the skulls correspond to the location of the craniofacial stabilization site, comprising the steps of:
   (a) selecting a craniofacial stabilization site on the human skull which is desired to be stabilized using the plate;
   (b) preparing a stamp that has been curved with non-uniform radii of curvature in each of the face dimension, cross sectional dimension and contour dimension to fit the structure and shape of craniofacial sites on a plurality of human skulls whose locations on the skulls correspond to the location of the craniofacial stabilization site;

(c) providing material for forming the plate; and (d) stamping the material to form an osteosynthesis plate that is contoured in three dimensions to fit the structure and shape of the craniofacial sites on the plurality of human skulls corresponding to the craniofacial stabilization site, by pressing the stamp against the entire top face and bottom face of the plate; and (e) after steps (a) through (d), placing the plate in packaging that identifies the craniofacial site for which the plate is contoured.

6. A method of manufacturing an osteosynthesis plate according to claim 5 further comprising the step of cutting the plate from the material, apart from the step of stamping the material.

7. A method of manufacturing an osteosynthesis plate according to claim 6 in which the step of cutting the plate from the material occurs before from the step of stamping the material.

8. A packaged osteosynthesis plate manufactured according to the method of claim 5.

* * * * *